United States Patent [19]

Sackner

[11] 4,456,015

[45] Jun. 26, 1984

[54] NON-INVASIVE METHOD FOR SEMIQUANTITATIVE MEASUREMENT OF NECK VOLUME CHANGES

[75] Inventor: Marvin A. Sackner, Miami Beach, Fla.

[73] Assignee: Respitrace Corporation, Ardsley, N.Y.

[21] Appl. No.: 364,710

[22] Filed: Apr. 2, 1982

Related U.S. Application Data

[63] Continuation-in-part of Ser. No. 266,850, May 26, 1981.

[51] Int. Cl.³ .............................................. A61B 5/08
[52] U.S. Cl. ................................... 128/721; 128/774
[58] Field of Search ............... 128/693, 694, 713, 725, 128/721–723, 670, 671, 716, 774

[56] References Cited

U.S. PATENT DOCUMENTS

| | | | |
|---|---|---|---|
| 2,649,573 | 8/1953 | Goldberg et al. | 128/782 X |
| 2,667,159 | 1/1954 | Goldberg et al. | 128/694 |
| 4,308,872 | 1/1982 | Watson et al. | 128/725 |
| 4,373,534 | 2/1983 | Watson | 128/725 |

*Primary Examiner*—Lee S. Cohen
*Attorney, Agent, or Firm*—Hubbell, Cohen, Stiefel & Gross

[57] ABSTRACT

A method of semiquantitatively measuring a subject's neck volume includes the steps of providing an extensible conductor in the form of a loop having a predetermined height; providing a signal variably responsive in value to changes in the inductance of the conductor; calibrating the signal by determining reference signal values obtained with the conductor disposed about at least two known volumes and using the reference signal values to establish the relationship between signal value and the volume enclosed by the conductor; disposing the conductor in close encircling relationship about the subject's neck; calibrating the signal for intrapleural pressure by using an invasive technique as a reference for determining a plurality of intrapleural pressures for the subject and simultaneously determining the signal value for each such intrapleural pressure measurment, thereby establishing the relationship between intrapleural pressure and signal value; discontinuing the reference technique; determining the signal value with the subject's airway closed, correlating the closed airway signal value with intrapleural pressure based on the established relationship between intrapleural pressure and signal value; and correlating intrapleural pressure obtained in accordance with the previous correlating step with the volume enclosed by the conductor based on the established relationship between signal value and enclosed volume.

5 Claims, 5 Drawing Figures

NON-INVASIVE METHOD FOR SEMIQUANTITATIVE MEASUREMENT OF NECK VOLUME CHANGES

CROSS REFERENCE TO RELATED APPLICATION

This application is a continuation-in-part of application Ser. No. 266,850 filed May 26, 1981 and entitled "Non-invasive Method for Monitoring Cardiopulmonary Parameters".

TECHNICAL FIELD

This invention pertains to a technique for semiquantitatively measuring neck volume changes and absolute neck volume on a non-invasive basis.

BACKGROUND ART

Measurement of cough effectiveness in patients with cough or retained secretions as a major symptom is clinically useful. This can be approximated by measurement of peak changes in intrapleural pressure during cough. A known technique for measuring intrapleural pressure utilizes an esophageal balloon catheter. While the esophageal balloon catheter serves its intended purpose, it requires placement in the subjects respiratory tract by insertion through the mouth, and thus constitutes an invasive technique. It will be readily apparent that such an invasive technique is not suited for long term or serial monitoring, which is often desirable in the case of patients with cough or retained secretions. It is therefore desirable to provide a non-invasive technique for semiquantitatively measuring intrapleural pressure during a cough.

DISCLOSURE OF THE INVENTION

In my copending application Ser. No. 266,850 entitled "Non-invasive Method for Monitoring Cardiopulmonary Parameters", I disclose one method for the non-invasive semiquantitative measurement of intrapleural pressure. In accordance with the method disclosed in that application, an extensible conductive loop is disposed about the subject's neck, and the loop is incorporated in the inductance element of an LC oscillator. As the subject breathes, the neck contracts and expands thereby varying the volume enclosed by the loop and hence the inductance of the loop. These inductance changes are reflected as changes in the frequency of the LC oscillator, and these frequency changes are then converted to a suitable voltage signal. In said application, it is hypothesized that there is a linear or predictable relationship between intrapleural pressure and the expansions and contractions of the neck as detected by the loop. Consequently, it is hypothesized that if the signal from the loop is initially calibrated by comparison with readings taken, for example, from an esophageal balloon catheter, then intrapleural pressure may be semiquantatively determined from subsequent readings by observing the percent change from baseline.

The disadvantages of this technique is that it does not allow for the clinical comparison of measurements taken on different occasions. This is especially true where different conductive loops and/or processing circuitry are used. Further, contraction of neck muscles and increases in neck volume due to displacement of blood from the superior vena cava to the neck veins during coughing and straining produces a measure which differs from intrapleural pressure. In accordance with the method of the present invention, this problem is overcome by calibrating the neck loop against known volume standards, such that each mouth pressure measurement during coughing and straining may be correlated with the actual volume enclosed by the loop. In coughing or straining pressure in the mouth against a closed shutter correlates with intrapleural pressure. With the data in this form, measurements taken on different occasions may be clinically compared.

BRIEF DESCRIPTION OF THE DRAWINGS

In the drawings, wherein like reference numerals represent like parts.

BEST MODE FOR CARRYING OUT THE INVENTION

In accordance with the method of the present invention, an extensible electrically conductive loop is disposed and held in close encircling relation about the neck. The ends of the loop are connected to circuits capable of providing a signal indicative of the changes in the inductance of the loop which, for small changes, is proportional to changes in the volume enclosed by the loop. By suitably processing the signal, a semiquantitative measurement of neck volume change during cough or straining may be obtained.

Figure 1:
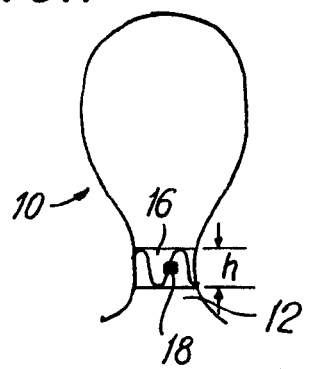
FIG. 1 is a perspective view showing a portion of the system for semiquantitatively measuring neck volume changes in accordance with the method of the present invention.

Referring now to FIG. 1, the extensible electrically conductive loop 14 disposed in close encircling relation about the neck 12 of the subject 10 is preferably supported in any suitable fashion on an elastic tube 16 or the like. The tube 16 preferably has two free ends (not shown) which may be releasably connected, as by Velcro strips, to facilitate placement about the neck 12. The conductive loop 14 is rendered extensible by, for example, forming the loop in alternating up and down looplets advancing in a plane. As shown in FIG. 1, this provides the loop 14 with a finite height h. Numerous other configurations for rendering a conductive loop extensible, and for securing the conductive loop to a tubular stretch bandage or the like, are disclosed in commonly assigned U.S. Pat. No. 4,308,872, the contents of which are hereby incorporated herein by reference in their entirety.

Changes in the cross sectional area of all or part of the neck portion enclosed by the loop 14 causes the elastic tube 16 and the conductive loop 14 to expand and contract. This results in corresponding changes in the cross sectional area of the effected portions of the loop 14, and hence in the inductance of the loop. As explained below, if the inductance of the loop 14 is converted to an electrical signal, a semiquantitative measurement of neck volume for the subject 10 may be obtained.

The preferred circuitry for converting the inductance of the loop 14 to a suitable electrical signal is described in detail in my commonly assigned copending application Ser. No. 317,418, entitled Surface Inductive Plethysmograph, the contents of which are hereby incorporated herein in their entirety. Suffice it to say that the loop 14 is incorporated in the inductance element of an LC oscillator diagrammatically illustrated in FIG. 1 at 18. By virtue of this arrangement, variations in the inductance of the loop result in corresponding changes in the frequency of the oscillator circuit. For small inductance changes, the change in the inductance of the loop 14 is proportional to the change in the output frequency of the oscillator. The frequency signal at the output of the oscillator circuit is then converted to a corresponding voltage signal, which may be displayed on one or more suitable output devices, such as a CRT or strip chart recorder.

In parent application Ser. No. 266,850, a technique is disclosed for calibrating the loop 14 when disposed about the subject's neck 12 for obtaining a semiquantitative measurement of intrapleural pressure for the subject 10. In accordance with that method, the loop 14 is disposed about the subject's neck 12 in the manner shown in FIG. 1. The subject's airway is then closed, as by a mouthpiece capable of recording mouth pressure, such as by incorporating a pressure transducer in the mouthpiece. Under these circumstances, i.e. closed airway, mouth pressure equals alveolar pressure, which closely approximates intrapleural pressure. The subject is then instructed to make graded expiratory efforts against the closed airway, and the mouth pressure (approximately equals intrapleural pressure) for each effort is then plotted versus the output voltage signal. In this way, the relationship between the output voltage signal and intrapleural pressure is obtained by drawing a line through the plotted points. With the mouthpiece then removed, it was hypothesized that any subsequent output signal could be correlated to a particular intrapleural pressure by reference to the plotted line, on the assumption that there was predicatable relation between intrapleural pressure and breathing or coughing.

As long as the relationship between the output signal and the volume enclosed by the loop 14 remains the same, the foregoing method as described in application Ser. No. 266,850 will yield consistent results. It will be apparent, however, that this relationship will not remain constant for measurements made on different occasions over a period of weeks, months, or even years. This will be especially so if different loops 14 and/or different processing circuitry are used on different occasions. In accordance with the present invention, I have now found that if the loop 14 is calibrated with reference to known volume standards, measurements taken on different occasions may be clinically compared.

Figure 2:
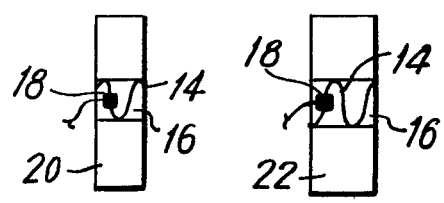
FIG. 2 is a perspective view showing one aspect of the calibration procedure.
Figure 3:
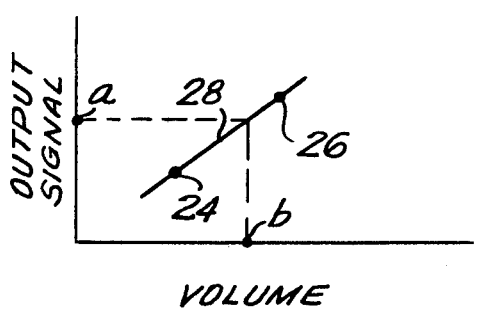
FIG. 3 is a graphical representation of the data points obtained by the procedure illustrated in FIG. 2.

More particularly, before placing the loop 14 about the subject's neck 12, the loop 14 is first calibrated by placement about two objects of known volume. For example, and referring to FIG. 2, the loop 14 may initially be placed about two cylinders 20, 22 having different known cross sectional areas, and the output voltage signal recorded for each placement. Clearly, once the cross sectional area of the cylinders 20, 22 is known, the volume enclosed by the loop 14 (A×h) is also known. With reference to FIG. 3, these two data points 24, 26 may be plotted on a graph wherein the abscissa is the volume enclosed by the loop 14 and the ordinate is the voltage output signal. For small volume changes of the type of interest here, the relationship between the output signal and the volume enclosed by the loop 14 may be approximated as linear. Accordingly, a line 28 may be drawn through the two data points 24, 26 on the graph of FIG. 3, whereupon any subsequent output signal value may be correlated to the actual volume enclosed by the loop 14 by reference to the line. For example, if a signal value a is obtained, then it is immediately known from the line 28 that the volume enclosed by the loop 14 is b.

Figure 4:
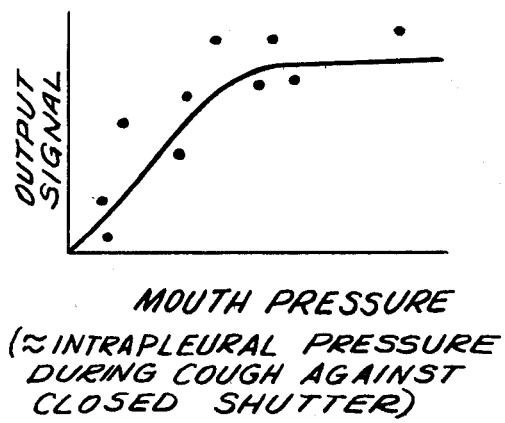
FIG. 4 is a graphical representation showing a further step in the calibration procedure.

After the loop 14 has been thus calibrated, it is transferred to the subject's neck 12. The subject 10 is then instructed to cough with graded degrees of effort against a closed airway. As noted earlier, when the subject's airway is closed, the mouth pressure approximates intrapleural pressure. During these graded efforts, the subject's mouth pressure is recorded, again as by employing a pressure transducer incorporated in a mouthpiece which also closes the subject's airway. For each effort, and as shown in FIG. 4, the output signal is plotted against the the recorded mouth pressure, resulting in a plurality of data points 30. From FIG. 4 it may be seen that the relationship between the volume enclosed by the loop 14 and intrapleural pressure is nonlinear. Accordingly, it is recommended that at least six to ten graded measurements be made, so that a line 32 drawn through the plotted points 30 accurately represents the relationship. At this point, the mouth piece may be removed, whereupon subsequent signals may be correlated to particular intrapleural pressures by reference to the line 32.

I have now recognized that such subsequent measurements are semiquantitatively accurate only under a closed airway condition, i.e. with the subject's glottis closed. This occurs, for example, during a cough, defecation or straining. For example, during a cough, the output signal is in the form of a spike, the rise time of the spike corresponding to the period when the glottis is closed. Consequently, by measuring the peak of the spike and transferring that reading to the line 32 in the graph of FIG. 4, a semiquantitative measurement of the intrapleural pressure may be obtained. I have verified that the technique yields semiquantitatively accurate data under the condition of a closed airway by simultaneous use of an esophageal balloon catheter.

Figure 5:
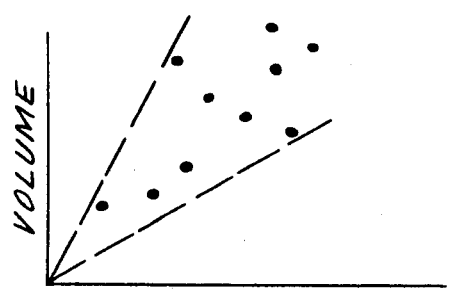
FIG. 5 is another graphical representation illustrating the relationship between intrapleural pressure during a cough and the volume enclosed within the conductive loop as obtained in accordance with the method of the present invention.

It will be apparent that once the loop 14 is calibrated, each measurement may also be correlated to a particular enclosed volume within the loop 14 by reference to the graph of FIG. 3. Accordingly, and as shown in FIG. 5, a graph may be drawn for the subject 10 wherein intrapleural pressure is plotted versus the volume enclosed within the loop 14, and it may be seen that the plot is accurate within about ±30%. The graph of FIG. 5 is highly useful, as it may be compared with similar graphs based on intrapleural measurements taken at other times, even if different loops 14 and/or different processing circuitry are used. This is so because the graph of FIG. 5 represents the relationship between intrapleural pressure and the actual volume enclosed by the loop 14, and hence is independent of the output signal value, which may vary for different loops 14 and/or different processing circuitry. The clinical usefulness of such comparisons will be apparent to those skilled in the art. Of course, the apparatus must be recalibrated in accordance with the procedure described above each time new measurements are taken. In fact, it may be desirable to recalibrate when a large number of measurements are taken during a single session, as this avoids innacuracies due, for example, to temperature drift, which are inherent in the use of electronic circuitry.

Once the foregoing description is known, various changes and modifications will suggest themselves to those skilled in the art. Accordingly, the above descritpion should be construed as illustrative and not in the limiting sense, the scope of the invention being defined by the following claims.

I claim:

1. A method of semiquantitatively measuring a subject's neck volume comprising:
providing an extensible conductor in the form of a loop having a predetermined height;
providing a signal variably responsive in value to changes in the inductance of the conductor;
calibrating the signal by determining reference signal values obtained with the conductor disposed about at least two known volumes and using said reference signal values to establish the relationship between signal value and the volume enclosed by the conductor;
disposing said conductor in close encircling relation about the subjects's neck;
calibrating said signal for intrapleural pressure by using an invasive technique as a reference for determining a plurality of intrapleural pressures for said subject, and simultaneously determining the signal value for each such intrapleural pressure measurement, thereby establishing the relationship between intrapleural pressure and signal value;
discontinuing the reference technique;
determining the signal value with the subjects's airway closed;
correlating said closed airway signal value with intrapleural pressure based on said established relationship between intrapleural pressure and signal value; and
correlating intrapleural pressure obtained in accordance with the previous step with the volume enclosed by the conductor based on the established relationship between signal value and enclosed volume.

2. The method according to claim 1, wherein said reference technique comprises employing an esophageal balloon catheter.

3. The method according to claim 1, wherein said reference technique comprises said subject coughing with graded efforts against a closed airway, and recording the mouth pressure of said subject for each graded effort.

4. The method according to claim 1, wherein the step of determining the signal value with the subject's airway closed comprises determining the signal value while the subject's glottis is closed.

5. The method according to claim 4, wherein the step of determining the signal value with the subject's airway closed comprises determining the signal value while the subject is coughing, straining or defecating.

* * * * *